United States Patent
Copps

(10) Patent No.: US 9,937,019 B1
(45) Date of Patent: Apr. 10, 2018

(54) SYSTEMS, APPARATUSES, AND METHODS FOR STABILIZING A SUBJECT DURING RADIATION THERAPY

(71) Applicant: Daniel P. Copps, Tarzana, CA (US)

(72) Inventor: Daniel P. Copps, Tarzana, CA (US)

( * ) Notice: Subject to any disclaimer, the term of this patent is extended or adjusted under 35 U.S.C. 154(b) by 258 days.

(21) Appl. No.: 14/692,574

(22) Filed: Apr. 21, 2015

(51) Int. Cl.
*A61N 5/10* (2006.01)
*A61C 7/08* (2006.01)

(52) U.S. Cl.
CPC ............. *A61C 7/08* (2013.01); *A61N 5/10* (2013.01); *A61C 2201/005* (2013.01); *A61N 2005/1097* (2013.01)

(58) Field of Classification Search
CPC ........ A61F 5/0003; A61F 5/0006; A61F 5/56; A61F 5/566; A61F 2005/563; A61C 7/08; A61C 7/36; A61C 5/14; A61C 2201/00; A61C 2201/005; A63B 23/032; A63B 71/085; A63B 2071/086; A63B 2071/088; A61N 2005/1095
USPC .......... 128/849–856, 898; 433/5, 6, 7, 8, 19, 433/24, 140; 601/38; 602/902; 482/11
See application file for complete search history.

(56) References Cited

U.S. PATENT DOCUMENTS

| | | | | |
|---|---|---|---|---|
| 1,613,384 A * | 1/1927 | Dobrik | ................. | A61C 9/0006 433/46 |
| 5,460,527 A * | 10/1995 | Kittelsen | ................. | A61C 5/00 128/859 |
| 6,244,269 B1 * | 6/2001 | Tyler | ....................... | A61F 5/566 128/859 |
| 6,379,147 B1 * | 4/2002 | Georgakis | ............ | A61C 9/0006 433/37 |
| 2006/0219250 A1 * | 10/2006 | Farrell | ................. | A63B 71/085 128/859 |
| 2007/0254256 A1 * | 11/2007 | Farrell | ..................... | A61C 7/08 433/6 |
| 2010/0021862 A1 * | 1/2010 | Mah | ..................... | G03B 42/042 433/140 |
| 2012/0231932 A1 * | 9/2012 | Rafih | ................... | A63B 71/085 482/11 |
| 2013/0068237 A1 * | 3/2013 | Herman | ................... | A61C 5/90 128/862 |
| 2013/0118507 A1 * | 5/2013 | Chappuis | ............... | A61B 17/24 128/859 |

(Continued)

*Primary Examiner* — Tarla Patel
(74) *Attorney, Agent, or Firm* — Daniel L. Dawes; Marcus C. Dawes

(57) ABSTRACT

An oral appliance may be used to stabilize a subject during radiation therapy. The body of the oral appliance may be configured to be secured within the subject's mouth in an as-used position. A handle of the oral appliance may extend from the subject's mouth during use. The body may comprise a first portion configured to engage maxillary teeth, a second portion configured to engage mandibular teeth, a tongue positioning component, and/or other components. The tongue positioning component may be configured to receive the subject's tongue when the oral appliance is in the as-used position and to facilitate positioning the subject's tongue in a predetermined location and/or orientation with respect to the oral appliance when in use. One or both of the first portion or second portion may be configured to displace corresponding mandibular teeth or maxillary teeth away from the body and/or tongue positioning component in the as-used position.

9 Claims, 10 Drawing Sheets

(56) References Cited

U.S. PATENT DOCUMENTS

| | | | |
|---|---|---|---|
| 2015/0040917 A1* | 2/2015 | Gottsch | A63B 71/085 128/862 |
| 2015/0079530 A1* | 3/2015 | Bergersen | A61C 7/08 433/6 |
| 2015/0327955 A1* | 11/2015 | Hanswirth | A63B 23/032 128/862 |

* cited by examiner

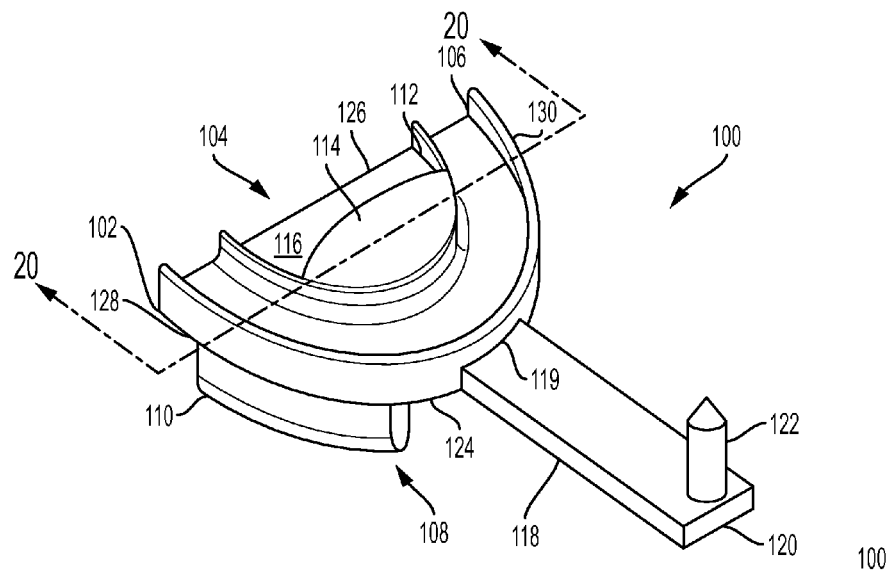
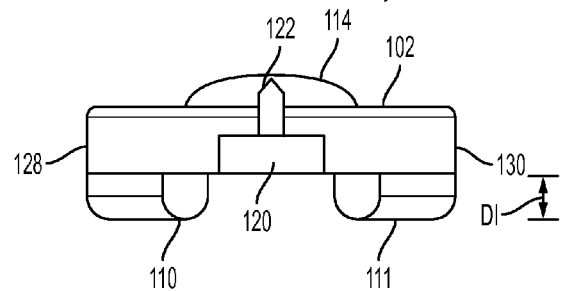
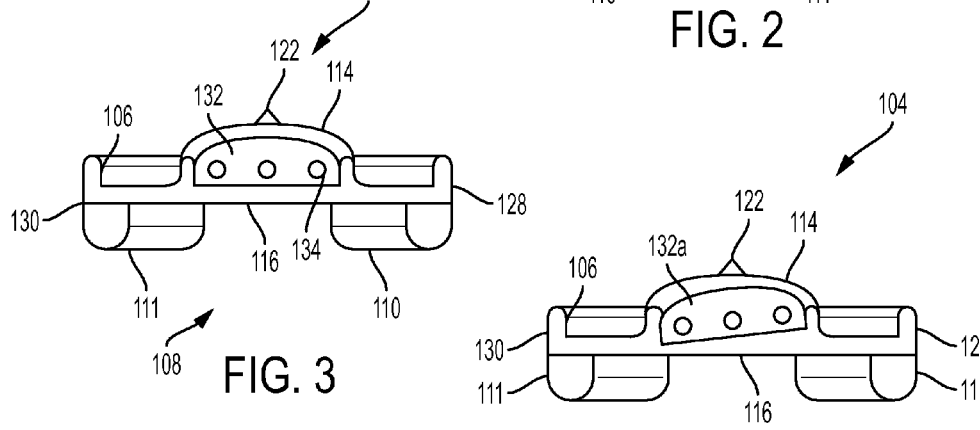
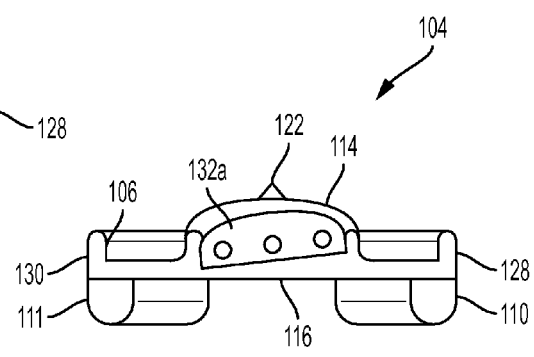

SYSTEMS, APPARATUSES, AND METHODS FOR STABILIZING A SUBJECT DURING RADIATION THERAPY

FIELD OF THE DISCLOSURE

This disclosure relates to systems, apparatuses, and methods for stabilizing a subject during radiation therapy.

BACKGROUND

Cancers of the face, mouth, head, and/or neck may require treatment with radiation therapy, such as Integrated Modular Radiation Therapy (IMRT) and/or other type of therapy. IMRT devices provide high precision in the application of radiation. A radiation oncologist, radiation therapist, and/or other practitioner of radiation therapy may achieve repeatable accuracy over the course of many sessions with the use of such devices. For example, in some cases, a subject may undergo thirty five sessions over the course of several weeks. It may be necessary to stabilize the subject's head, neck, and/or other body parts in the same or similar position for each session to ensure the repeatable accuracy in the application of radiation. Stabilization may be accomplished by restraining apparatuses which may facilitate positioning the head and/or neck in predetermined locations and/or orientations.

The application of radiation therapy to areas at or near a subject's mouth may cause restorations of one or more teeth (e.g., metal and/or other material fillings, and/or other restorations) to be heated by incoming radiation. When heated, surrounding soft tissues may inadvertently come into contact with the restorations and become burned or seriously injured.

SUMMARY

One aspect of the disclosure relates to an intraoral tissue positioning appliance (herein "the oral appliance") configured for stabilizing a subject during radiation therapy. The oral appliance may be configured to facilitate intraoral tissue positioning and/or other features or functions. In an as-used position of the oral appliance in a subject's mouth, the oral appliance may facilitate positioning one or more tissues of the mouth in a predetermined location and/or orientation during application of radiation therapy. The predetermined location and/or orientation of one or more tissues may be repeatedly achievable over subsequent uses of the oral appliance. In some implementations, tissue positioning may be related to isolating one or more restorations disposed in one or more teeth from soft tissues of the mouth.

In some implementations, the oral appliance may be configured to reposition hard and/or soft tissues to keep one or more tissues out of a primary beam of radiation. In some implementations, the oral appliance may be configured to hold a given tissue in the primary beam of radiation. By way of non-limiting example, if a cancer is in the cheek, an oral appliance may be configured to push the cheek out to isolate it and/or to move the tongue, teeth, and/or other tissues out of the primary beam of radiation that may be directed toward the cheek.

In some implementations, intraoral tissue positioning may be facilitated by one or more of separating the subject's mandibular teeth from their maxillary teeth, directly covering one or more restorations with one or more parts of the oral appliance, displacing soft tissues away from one or more teeth in a predetermined location and/or orientation, and/or other techniques for intraoral tissue positioning. With the oral appliance in an as used position in a subject's mouth, the oral appliance may facilitate keeping movable tissues of the mouth in stabile positions. A practitioner (e.g., radiation oncologist and/or other practitioner) may confidently carry out radiation therapy to targeted areas of the face, mouth, neck, and/or head without inadvertently injuring soft tissues.

In some implementations, the oral appliance may comprise a body, a handle, and/or other components. The body may be configured to be secured within the subject's mouth in an as-used position of the oral appliance. The body may comprise one or more of a first portion configured to engage one or more maxillary teeth and/or gums of the subject, a second portion configured to engage one or more mandibular teeth and/or gums of the subject, the second portion being positioned opposite the first portion, a tongue positioning component, and/or other components. The tongue positioning component may be configured to receive the subject's tongue when the oral appliance is in the as-used position. The tongue receiving component may be configured to facilitate positioning the subject's tongue in a predetermined location and/or orientation with respect to the oral appliance when in the as-used position.

In some implementations, one or both of the first portion and/or second portion may be configured to displace corresponding mandibular teeth and/or gums or maxillary teeth and/or gums away from the body of the oral appliance when the oral appliance is in the as-used position. By way of non-limiting example, the oral appliance may be configured such that a subject's lower jaw and upper jaw may be held open a predetermined distance.

The handle may be attached to a first end of the body. The handle may extend from the first end of the body. The handle may be configured to extend to an exterior of the subject's mouth when the oral appliance is in the as-used position.

One aspect of the disclosure relates to a system for stabilizing a subject during radiation therapy. The system may comprise an intraoral tissue positioning appliance (herein "the oral appliance"), a head restraint, and/or other components. The oral appliance may comprise a body, a handle, and/or other components. The body may be configured to be secured within the subject's mouth in an as-used position of the oral appliance. The body may comprise one or more of a first portion configured to engage one or more maxillary teeth and/or gums of the subject; a second portion configured to engage one or more mandibular teeth and/or gums of the subject, the second portion being positioned opposite the first portion; a tongue positioning component; and/or other components. The tongue positioning component may be configured to receive the subject's tongue when the oral appliance is in the as-used position. The tongue receiving component may be configured to facilitate positioning the subject's tongue in a predetermined location and/or orientation with respect to the oral appliance when in the as-used position.

In some implementations, one or both of the first portion and/or second portion may be configured to displace corresponding mandibular teeth and/or gums or maxillary teeth and/or gums away from the body of the oral appliance when the oral appliance is in the as-used position.

The handle may be attached to a first end of the body. The handle may extend from the first end of the body. The handle may be configured to extend to an exterior of the subject's mouth when the oral appliance is in the as-used position.

The head restraint may comprise a first surface configured to engage at least a portion of the subject's face in a second as-used position of the head restraint, a second surface opposite the first surface, an aperture communicating between the first surface and second surface and positioned to align with the mouth of the subject when the head restraint is in the second as-used position, and/or other components. In some implementations, the handle of the oral appliance in the as-used position of the oral appliance may extend through the aperture of the head restraint when the head restraint is concurrently in the second as-used position.

These and other features and characteristics of the present technology, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and in the claims, the singular form of "a", "an", and "the" include plural referents unless the context clearly dictates otherwise.

BRIEF DESCRIPTION OF THE DRAWINGS

FIG. 1 illustrates an exemplary implementation of an oral appliance configured for stabilizing a subject during radiation therapy.

FIG. 2 illustrates first end view of the oral appliance of FIG. 1.

FIG. 3 illustrates a second end view of the oral appliance of FIG. 1.

FIG. 4 illustrates a view of an implementation of a cavity of a tongue positioning component of an oral appliance.

DETAILED DESCRIPTION

Figure 5:
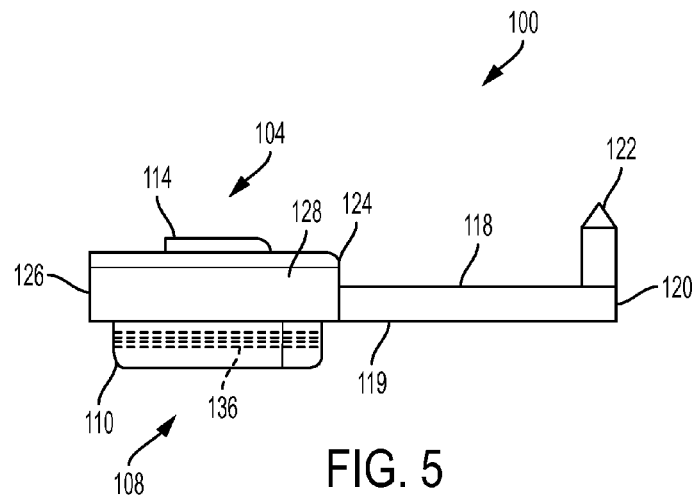
FIG. 5 illustrates a side view of the oral appliance of FIG. 1.
Figure 6:
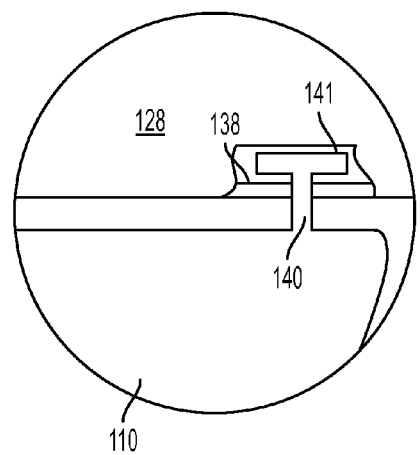
FIG. 6 illustrates an implementation of the oral appliance of FIG. 1, including slidable attachment of a protrusion to the body of the oral appliance.
Figure 7:
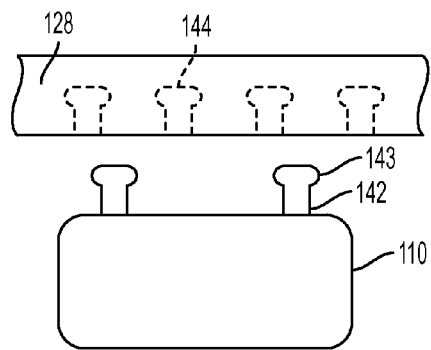
FIG. 7 illustrates an implementation of the oral appliance of FIG. 1, including removable attachment of a protrusion to the body of the oral appliance.

One or more implementations of an oral appliance (see, e.g., oral appliance 100 in FIG. 1, oral appliance 200 in FIG. 8, oral appliance 300 in FIG. 11, oral appliance 400 in FIG. 14, and/or other implementations) may be configured to stabilize a subject during radiation therapy. One or more implementations of the oral appliance (100, 200, 300, 400, and/or other implementations) may be configured to facilitate stabilizing a subject's lips, jaw, tongue, cheeks, and/or other parts of a subject's mouth and/or head during radiation therapy and/or to facilitate other intraoral tissue positioning. By way of non-limiting example, the oral appliance may be adapted to be bit down on by a user in the as-used position to keep moving parts of the subject's mouth (e.g., lips, jaw, tongue, cheeks, and/or other parts) in stabile positions and/or orientations within the mouth.

One or more implementations of the oral appliance (100, 200, 300, 400, and/or other implementations) may be configured to facilitate isolating one or more mandibular and/or maxillary teeth of the subject from soft tissues of the mouth during radiation therapy, separate the mandibular teeth from the maxillary teeth (e.g., separate the lower jaw from the upper jaw), and/or facilitate other operative intraoral tissue positioning. In particular, one or more implementations of the oral appliance (100, 200, 300, and/or 400) may facilitate isolating one or more teeth having metal, and/or other material dental restorations from soft tissues of the mouth.

During radiation therapy, metal and/or other dental restorations may be heated by incoming radiation and/or may produce backscatter. The heating of a given restoration and/or backscatter produced from the restoration may cause damage to soft tissues adjacent to the given restoration. Thus, by isolating one or more teeth and/or one or both of the dental arches from other tissues in the oral cavity, a practitioner (e.g., radiation oncologist) may confidently carry out radiation therapy to targeted areas without inadvertently injuring soft tissues. In some implementations, soft tissues which may be of concern may include inner surfaces of the cheeks, the tongue, lips, gums, palate, throat, and/or other soft tissues. By way of non-limiting example, for treating cancer of the cheek, it may be desired to displace the check away from buccal surfaces of one or more teeth.

FIGS. 1-7 illustrate various views of an exemplary implementation of an oral appliance 100 configured for stabilizing a subject during radiation therapy. In some implementations, the oral appliance 100 may comprise a body 102, a handle 118, and/or other components. The body 102 may be configured to be secured within the subject's mouth in an as-used position (see, e.g., FIG. 16) of the oral appliance 100. By way of non-limiting example, the body 102 may be substantially U-shaped and/or otherwise configured to conform to one or more of the maxillary dental arch, mandibular dental arch, palate, and/or other parts of a subject's mouth.

In some implementations, one or more portions of the body 102 may be shaped, sized, and/or otherwise configured to a "general" or "universal" configuration which may be suitable for use with the general populous. For example, a curvature and/or other aspects of the body 102 may be configured in accordance with a statistical average mouth shape for an adult (or child) of a particular region of the world. In some implementations, one or more portions of the body 102 and/or handle 118 may be shaped, sized, and/or otherwise configured to generic and/or universal prefabricated sizes including one or more of small, medium, large, and/or other prefabricated sizes.

In some implementations, one or more portions of the body 102 may be custom formed for a given subject. By way of non-limiting example, one or more portions of the body 102 may be custom formed based on bite impressions of a subject. In accordance with one or more methods of construction of the body 102, the one or more parts of the body 102 may be customized for an individual subject by a qualified dental professional by molding impressions of the teeth and/or recording bite position. A dental laboratory may fabricate one or more parts of the body 102 based on the data provided by the bite impressions. The above example of a custom formed oral appliance is provided for illustrative purposes only and is not to be considered limiting. For example, in some implementations, the use of generic sizes of the oral appliance may be preferred over custom formed ones. In some locations custom forming may not be available and/or cost effective. By having generic sizes, a practitioner may be able to offer the appliance to a wide range of subjects without the need for custom forming.

The body 102 and/or handle 118 may comprise radiolucent material and/or other materials that may produce no or insignificant amounts of radiation backscatter during radiation therapy. Materials may include one or more thermoplastic composites; tissue-equivalent materials such as polyurethane, acrylic, and/or other tissue-equivalent materials; and/or other materials. By way of non-limiting illustration, an exemplary cross-sectional view of the oral appliance 100 along line 20-20 of FIG. 1 is shown in FIG. 20.

Figure 20:
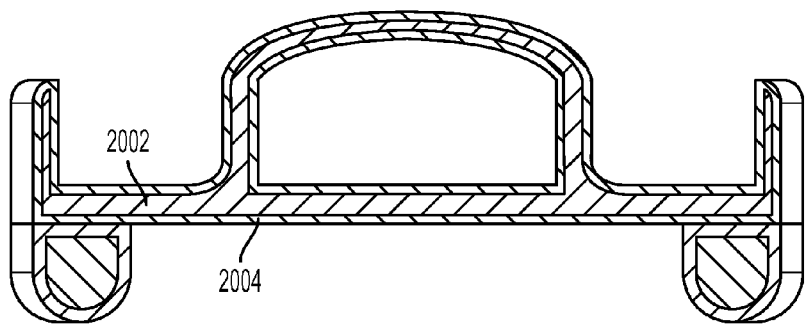
FIG. 20 shows an exemplary cross-sectional view of an oral appliance.

Referring now to FIG. 20, the body 102, handle 118, and/or other parts of oral appliance 100 may have a core 2002, an outer coating 2004, and/or other components. The core 2002 may be formed from radiolucent material and/or other material. The coating 2004 may comprise a material that provides a comfortable fit or texture of the oral appliance 100 in the subject's mouth. By way of non-limiting example, the coating 2004 may comprise a wax, silicon, thermally responsive material, radiolucent material, and/or other materials. A wax may include carnauba wax, and/or other type of wax. In some implementations, the coating 2004 may comprise a thermally responsive material that may facilitate a "boil-and-bite" type customization of the oral appliance 100. By way of non-limiting example, the coating 2004 may comprise ethylene-vinyl acetate and/or other thermally responsive material. In some implementations an average thickness of the core 2002 may be in the range of one to five millimeters and/or other range. In some implementations, an average thickness of the coating 2004 may be in the range of one to three millimeters and/or other range.

Returning to FIG. 1, the body 102 may comprise a first end 124, a second end 126 opposite the first end 124, a first side 128, a second side 130 opposite the first side 128, a first portion 104, a second portion 108 opposite the first portion 104, a tongue positioning component 112, and/or other components. In some implementations, the handle 118 may comprise a proximal end 119, a distal end 120 opposite the proximal end 119, and/or other components. In some implementations, the proximal end 119 of the handle 118 may be attached to first end 124 of the body 102 and/or may be attached to the body 102 in other ways.

In some implementations, the proximal end 119 of the handle 118 may be rigidly attached to the first end 124 of the body 102. By way of non-limiting example, the handle 118 may be attached to the body 102 via an adhesive, a resin, welding, and/or by other attachment methods. In some implementations, the handle 118 may be removably attached to the body 102. For example, the proximal end 119 of the handle 118 may removably attach to the body 102 via a removable mechanical coupling device and/or other device facilitating removable attachment. A mechanical coupling device may include snap fits, magnets, and/or other mechanical coupling device. In some implementations, the oral appliance 100 (e.g., handle 118 and body 102) may be formed from a unitary piece of material. For example, the oral appliance 100 may be formed by subtractive manufacturing methods, 3D printing, and/or formed in other ways.

In some implementations, the handle 118 may facilitate positioning the oral appliance 100 into an as-used position in a subject's mouth. The subject and/or a practitioner applying radiation therapy may position and/or orient the oral appliance 100 in the subject's mouth via the handle 118. For sanitation and/or other purposes, the subject and/or practitioner may not have to physically touch the body 102 and/or other parts of the oral appliance 100 that may come into contact with tissues of the subject's mouth. In some implementations, once positioned, the handle 118 may be removed (given that the implementation of the oral appliance facilitates removable attachment). Further, if a subject may be required to remove and/or replace the oral appliance 100 multiple times, the handle 118 may generally facilitate user-friendly handling of the oral appliance 100. It is noted that implementations of the oral appliance (100, 200, 300, 400, and/or other implementations) may be configured without a handle while not departing from the scope the disclosure.

Figure 17:
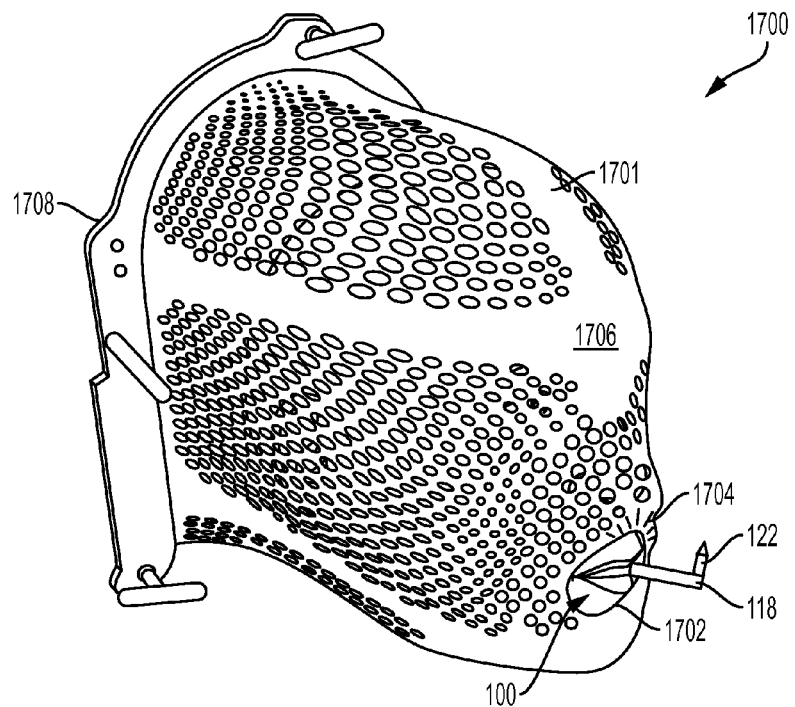
FIG. 17 illustrates a system for stabilizing a subject during radiation therapy, including a head restraint and oral appliance, in accordance with one or more implementations.

In some implementations described in more detail herein, the handle 118 may further facilitate registering a position and/or orientation of the oral appliance 100 with respect to a head restraint (see, e.g., FIG. 17). In some implementations, a system configured for stabilizing a subject during radiation therapy may comprise an oral appliance and a head restraint (see, e.g., FIG. 17). In some implementations, the handle 118 may include a registration component 122 disposed at the distal end 120 (see, e.g., FIG. 1). The registration component 122 may facilitate visually registering a position and/or orientation of an oral appliance in an as-used position in a subject's mouth relative to a head restraint in an as-used position supporting the subject's face, neck, and/or head.

In FIGS. 1-7, the first portion 104 of the body 102 may be configured to engage one or more maxillary teeth, gums, palate, and/or other parts of the subject's mouth in the as-used position of the oral appliance 100. By way of non-limiting example, the first portion 104 may be configured as a palatal portion of the oral appliance 100. In some implementations, one or both of the first portions 104 and/or second portion 108 may comprise channels shaped to conform to a corresponding mandibular dental arch and/or maxillary dental arch. By way of non-limiting example, as shown in FIG. 1, the first portion 104 may include a first channel 106. The first channel 106 may be shaped to conform to at least part of a maxillary arch of a subject.

In some implementations, the second portion 108 may be configured to engage one or more mandibular teeth, gums, and/or other parts of the subject mouth in the as-used position of the oral appliance 100. For example, the second portion 108 may be configured as the mandibular portion of the oral appliance 100.

In some implementations, one or both of the first portion 104 and/or second portion 108 may be configured to displace corresponding mandibular teeth and/or gums or maxillary teeth and/or gums away from the body 102 and/or tongue positioning component 112 of the body 102 when the oral appliance 100 is in the as-used position. By way of non-limiting example, one or both of the first portion 104 and/or second portion 108 may include one or more protrusions that protrude from the body 102 one or more predetermined distances. By way of non-limiting example, when in the as-used position, the subject may bite down on the oral appliance 100 such that one or more teeth may come into direct contact with one or more protrusions, thereby securing the oral appliance 100 in the subject's mouth and displacing a corresponding one or more maxillary and/or mandibular teeth and/or gums away from the body 102. In some implementations, the displacement of one or more teeth may generally cause the user's mouth to be maintained in an opened position a predetermined distance.

In FIG. 2, the second portion 108 of the body 102 of oral appliance 100 may include a first protrusion 110, a second protrusion 111, one or more other protrusions, and/or other components. The first protrusion 110, the second protrusion 111, and/or other protrusions may be shaped to conform to the curvature of the body 102. The first protrusion 110 may be positioned adjacent the first side 128 of the body 102. The second protrusion 111 may be positioned adjacent the second side 130 of the body 102. In some implementations, the positioning and/or orientation of the first protrusion 110 with respect to the body 102 may mirror the positioning and/or orientation of the second protrusion 111.

In some implementations, the first protrusion 110, second protrusion 111, and/or other protrusions may have predetermined thicknesses "D1." During operative engagement of one or more mandibular teeth and/or gums of the subject with corresponding first protrusion 110 and/or second protrusion 111 in the as-used position (e.g., FIG. 16), the subject's mandible may be displaced the corresponding distance "D" from the body 102.

In some implementations, one or more protrusions may be operatively positioned on a portion of the body 102 such that a given protrusion may engage one or more predetermined maxillary and/or mandibular teeth of the subject and/or parts of the subject's gums when in an as-used position. For example, one or more protrusions may be formed on the body 102 based on locations of restorations in one or more of the subject's teeth. In particular, the body 102 may be formed such that a given protrusion may come into direct contact with one or more given teeth having restorations when in the as-used position. Such positioning of one or more protrusions may ensure that one or more teeth having restorations may be covered by the oral appliance 100. Soft tissues of the mouth may be prevented from coming into direct contact with the restorations when the oral appliance 100 is in the as-used position during radiation therapy. One or more protrusions in direct contact with one or more restorations may act as a heat sink for the restorations should they become heated during the course of the therapy.

It is noted that a quantity, positioning, orientation, thickness, and/or other attributes of one or more protrusions of the body 102 may be determined by a practitioner and/or other designer of the oral appliance 100 based on needs of a subject and/or an area where radiation therapy may be applied. By way of non-limiting example, in some implementations, a given thickness "D" of a given protrusion may be in the range of one to thirty millimeters and/or other range. In some implementations, a given thickness of a given protrusion may be approximately five millimeters and/or other thickness.

Figure 16:
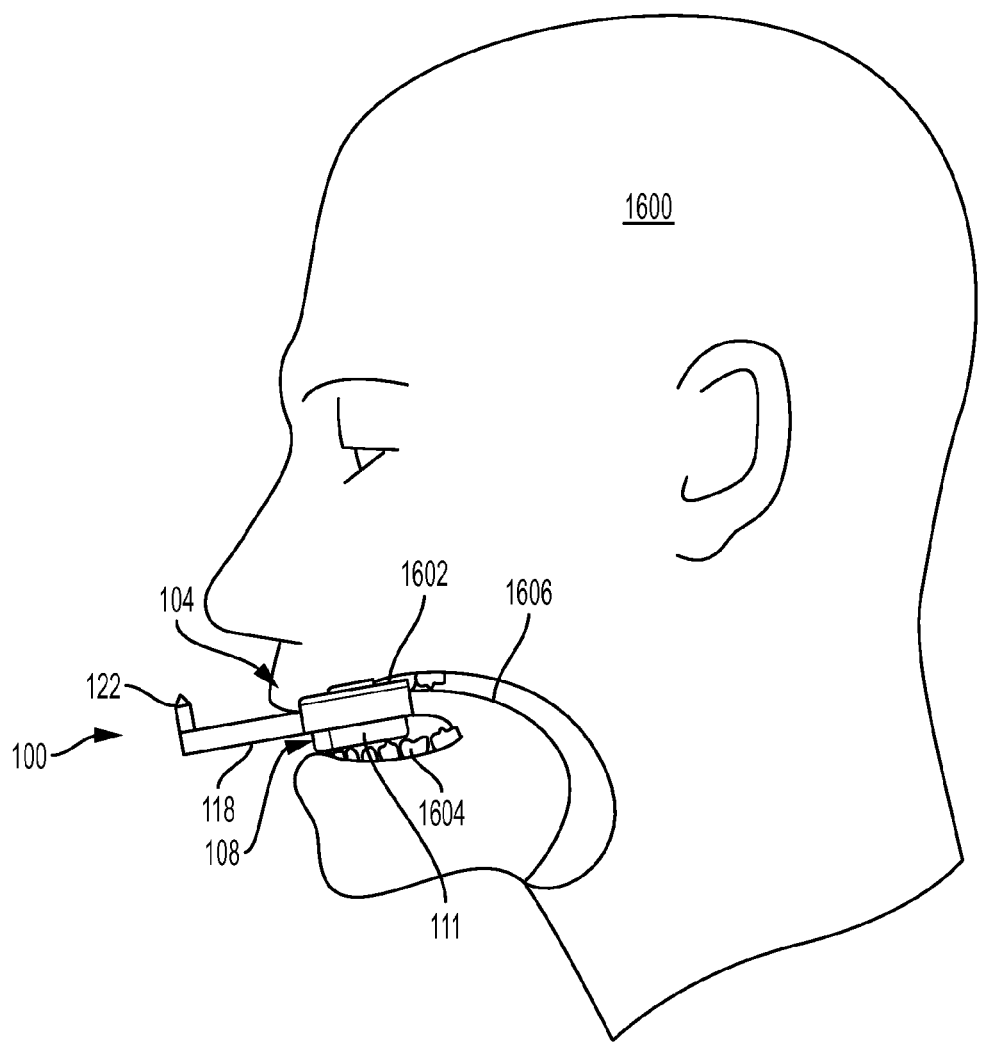
FIG. 16 illustrates the oral appliance of FIG. 1 in an exemplary as-used position.

In an exemplary as-used position of the oral appliance 100 in FIG. 16, the first portion 104 may be configured to engage one or more maxillary teeth 1602, gums, palate, and/or other parts of the mouth of a subject 1600. By way of non-limiting example, the first channel 106 (not shown in FIG. 16) may be configured to conform to at least part of the subject's maxillary dental arch. The second portion 108 may be configured to engage one or more mandibular teeth 1604, gums, and/or other parts of the mouth of the subject 1600 in the as-used position of the oral appliance 100. Further, the tongue positioning component 112 (not labeled in FIG. 16) may be configured to receive the subject's tongue 1606. The tongue positioning component 112 may be configured to facilitate positioning the subject's tongue 1606 in a predetermined location and/or orientation with respect to the oral appliance 100 and/or subject's mouth when in the as-used position. For example, the oral appliance 100 may be configured to facilitate positioning the subject's tongue 1606 in a location that is away from the mandibular teeth 1604 (e.g., determined by the thickness of one or more protrusions). The second protrusion 111 is currently shown in FIG. 16. The handle 118 may extend from the subject's mouth in the as-used position of the oral appliance 100, substantially as shown in the figure.

In some implementations, as illustrated in FIG. 5, one or more protrusions (e.g., first protrusion 110) may include one or more score lines 136, indicia, and/or other markings that may facilitate sizing a given protrusion. For example, a given score line 136 may denote a given thicknesses of a protrusion corresponding to a desired displaced distance from the body 102 when in the as-used position. A practitioner may size the protrusions as needed by one or more of cutting, shaving, sanding, and/or otherwise removing portions of the protrusion while referencing a desired score line 136.

In some implementations, a positioning of a given protrusion (e.g., first protrusion 110) relative to the first end 124 and/or second end 126 of the body 102 may be adjustable. In some implementations, adjustability of a given protrusion may be facilitated by slidable attachment, removable attachment, and/or other techniques facilitating adjustable attachment of a given protrusion to the body 102. Changing a position of a protrusion may change the distance a subject's mouth is maintained open when the oral appliance 100 is in the as-used position. By way of non-limiting example, by moving one or more protrusions toward the second end 126, the oral appliance 100 may cause the subject's mouth to open wider than when positioning one or more protrusions toward the first end 124.

In some implementations, slidable attachment may be facilitated by one or more supports of a given protrusion being engaged within a given channel, or track, disposed on or in the body 120, and/or by other techniques for facilitate slidable attachment of a protrusion relative the body 102. By way of non-limiting illustration in FIG. 6, the first protrusion 110 may include one or more posts 140 and/or other components. A given post 140 may include a flanged end 141, and/or other components. The flanged end 141 may be configured to be engaged within a channel 138 disposed in or on the body 102 (the channel 138 currently being shown by a cut-away portion of the body 102 adjacent the first side 128). A given channel 138 may be disposed adjacent a corresponding first side 128 and/or second side 130. A given channel 138 may run the length, or a portion of the length, of the body 102 from the first end 124 to the second end 126. The flanged end 141 may be configured to translate within the channel 138, thereby facilitating slidable attachment of a given protrusion to the body 102. Slidable attachment may be accomplished in other ways suitable for the purposes describe herein.

In some implementations, removable attachment may be facilitated by one or more removable fastening devices including one or more of snap fits, hook and loop fasteners, and/or other removable fastening devices. By way of non-limiting illustration in FIG. 7, an exemplary snap-fit-type removable attachment of the first protrusion 110 to the body 102 is shown. The first protrusion 110 and/or other protrusion may include one or more posts 142 and/or other components. A given post 142 may include a flanged end 143 and/or other components. The body 102 of the oral appliance 100 may include one or more post receiving cavities 144 (depicted by dashed lines) disposed in the body 102. The one or more post receiving cavities 144 may be disposed adjacent the first side 128 and/or second side 130 in a mirrored configuration. A given post receiving cavity 144 may be configured with a shape that is the same or similar to a given post 142 of a given protrusion. A given post 142 may be configured to snap fit, friction fit, and/or other be received into a corresponding post receiving cavity 144. In some implementations, multiple post receiving cavities 144 and/or sets of post receiving cavities 144 may be disposed and/or arranged such that multiple positions of a given protrusion with respect to the body 102 may be achieved.

In some implementations, the oral appliance 100 may be configured such that the first portion 104 may include one or more protrusions that displace the maxillary teeth from the body 102, while the second portion 108 may include a channel shaped to conform to the mandibular dental arch. In such implementations, the subject's maxillary teeth, gums, and/or palate may be displaced from the body 102 a distance corresponding to a thickness of one or more protrusions. Other variations within the scope of this disclosure are also contemplated.

Returning to FIG. 1, the tongue positioning component 112 may be configured to receive the subject's tongue when the oral appliance 100 is in the as-used position. As shown in FIG. 16, the tongue positioning component 112 (not labeled in FIG. 16) may be configured to facilitate positioning the subject's tongue 1606 in a predetermined location and/or orientation with respect to the oral appliance 100 and/or subject's mouth when in the as-used position. By way of non-limiting example, the tongue positioning component 112 may be configured to position and/or orient the tongue in a desired location and/or orientation within the subject's mouth during use of the oral appliance 100 to prevent the tongue from coming into contact with one or more teeth, an incoming primary beam of radiation, and/or backscatter radiation produced from restorations of the teeth; to hold the tongue in a primary beam of radiation, and/or for other intraoral tissue positioning.

Referring now to FIG. 3, the tongue positioning component 112 may comprise a tongue receiving cavity 132 and/or other components. The tongue receiving cavity 132 may be configured to receive the subject's tongue when the oral appliance 100 is in the as-used position. The tongue receiving cavity 132 may be formed by a first sidewall 114, a second sidewall 116, and/or other sidewalls. The tongue positioning component 112 may be configured such that the tongue may be seated within the tongue receiving cavity 132 between the first sidewall 114, second sidewall 116, and/or other sidewalls of the tongue receiving cavity 132 during the as-used position of the oral appliance 100 in the subject's mouth. In some implementations, the first sidewall 114 may be curved.

In some implementations, the tongue receiving cavity 132 may be configured to facilitate positioning the subject's tongue in a predetermined target location and/or orientation of the tongue with respect to the body 102 of the oral appliance 100 when in use. In some implementations, a target location and/or orientation may correspond to positioning and/or orientating the tongue toward or away from one or more of the first end 124, the second end 126, the first side 128, the second side 130, the first portion 104, and/or the second portion 108. A target location and/or orientation may be a location and/or orientation determined by a practitioner based on the needs of a subject, and/or other information.

By way of non-limiting example, the tongue positioning component 112 may be configured to position the tongue at a first target location and/or orientation. The first target location and/or orientation may be related to the tongue being one or more of: medially positioned (e.g., centered within the subject mouth), anteriorly positioned (e.g., adjacent the first end 124), posteriorly positioned (e.g., adjacent the second end 126), laterally positioned (e.g., adjacent one of the first side 128 and/or second side 130), and/or in one or more other positions.

In some implementations, obtaining desired anterior and/or posterior positioning of a subject's tongue by the tongue positioning component 112 may be facilitated by configuring a predetermined depth of the tongue positioning component 112 (e.g., depth of the tongue receiving cavity 132). In some implementations, obtaining desired lateral positioning of a subject's tongue may be facilitated by configuring the tongue positioning component 112 (e.g., tongue positioning cavity 132) closer to one of the first side 128 and/or second side 130. It is it to be understood that other changes to the configurations of the oral appliance 100 may be made as needed to achieve a desired intraoral tissue positioning.

In FIG. 3, in some implementations, the tongue positioning component 112 may include one or more feedback components 134 configured to provide tactile, gustatory, and/or other feedback to the subject. The one or more feedback components 134 may be configured to provide feedback to the subject when the oral appliance is in the as-used position and/or when the tongue is received by the tongue positioning component 112 (e.g., within tongue receiving cavity 132). Feedback provided by one or more feedback components 134 may relate to a location and/or orientation of the tongue within the tongue receiving cavity 132.

By way of non-limiting example, a given feedback component 134 may comprise a tactile protrusion extending from one or more sidewalls 114, 116 of the tongue receiving cavity 132. A tactile protrusion may comprise, for example, a raised bump extending from a sidewall. A given tactile protrusion may be positioned within the tongue receiving cavity 132 to correspond to one or more target locations a practitioner may desire to have a subject's tongue located.

By way of non-limiting example, one or more portions of the subject's tongue may come into contact with a tactile protrusion to signify that the tongue may correctly be in a target position. If the subject is unable to identify a contact of their tongue with a given protrusion, the subject may be instructed to continue to reposition their tongue within the tongue receiving cavity 132 until desired contact is made.

By way of non-limiting example, if a forward-most anterior positioning of the tongue within the tongue receiving cavity 132 is desired, a tactile protrusion may be disposed on a part of a sidewall of the tongue receiving cavity 132 closest to the first end 124 of the body. When a subject inserts their tongue into the tongue receiving cavity 132 when the oral appliance 100 is in the as-used position, the tip or other portion of the subject's tongue may come into contact with the tactile protrusion to indicate that they have obtained the target location of their tongue within the tongue receiving cavity 132 (e.g., positioned at the forward-most end of the cavity). The provision of one or more tactile protrusions providing feedback may similarly be carried out with respect to lateral positioning and/or other positioning of the tongue. One or more tactile protrusions may be disposed at various locations on one or more sidewalls of the tongue receiving cavity 134 as deemed suitable by a designer of the oral appliance 100 for providing feedback to a user with respect to one or more desired target locations.

In some implementations, a tongue receiving cavity 132 may be configured to a general and/or universal size in compliance with a statistical average length, width, and/or thickness of an adult (or child) tongue. For subjects who may have relatively smaller tongues, there may be empty space present within the tongue receiving cavity 132 when their tongue is received therein. This may make it difficult to discern whether the tongue is in a desired target location. As an exemplary solution, one or more feedback components 134 may be positioned at lateral sides of the tongue receiving cavity 132, a forward-most point in the tongue receiving cavity 132, and/or other points in the tongue receiving cavity 132 such that the user may be able to register the location of their tongue within the tongue receiving cavity 132 to ensure desired positioning.

In some implementations, gustatory feedback by one or more feedback components 134 may be facilitated by imbedding, attaching, and/or otherwise providing gustatory components within one or more sidewalls of the tongue receiving cavity 132.

A gustatory component may include, for example, a small mint and/or other components.

Referring now to FIG. 4, in some implementations, a cavity 132a of a tongue positioning component 112 of an oral appliance 100 may be configured to receive a subject's tongue at an angle with respect to a transvers axis of the tongue. By way of non-limiting example, the cavity 132a may be relatively inclined toward one of the first side 128 or second side 130 of the body 102 of the oral appliance 100. One or more configurations of the cavity 132a of this type may facilitate displacing a given side edge of the subject's tongue from the body 102 a predetermined distances and/or at a predetermine angle. Other variations of the tongue receiving cavity 132 and/or 132a are also contemplated.

Figure 8:
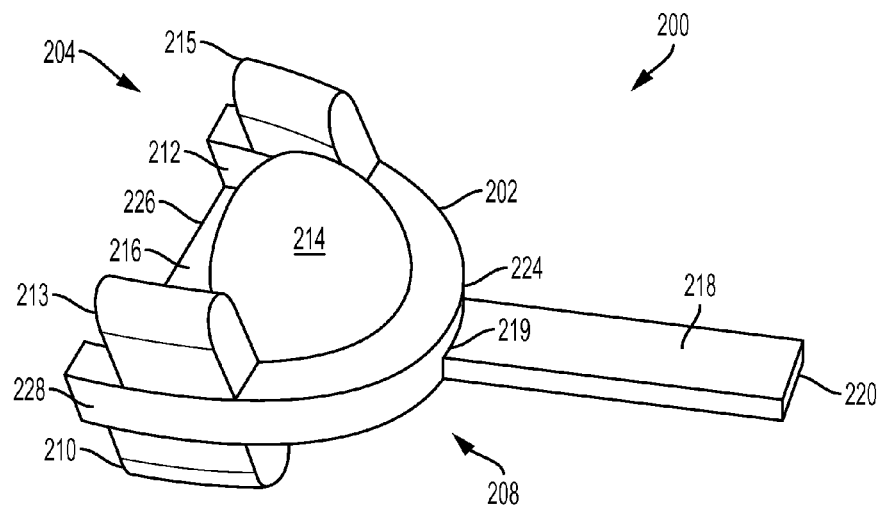
FIG. 8 illustrates another exemplary implementation of an oral appliance configured for stabilizing a subject during radiation therapy.
Figure 9:
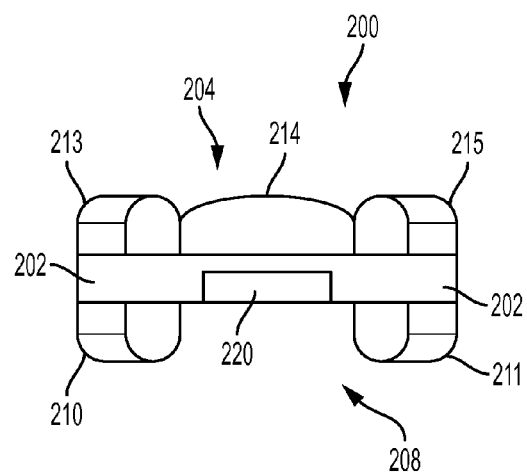
FIG. 9 illustrates a first end view of the oral appliance of FIG. 8.
Figure 10:
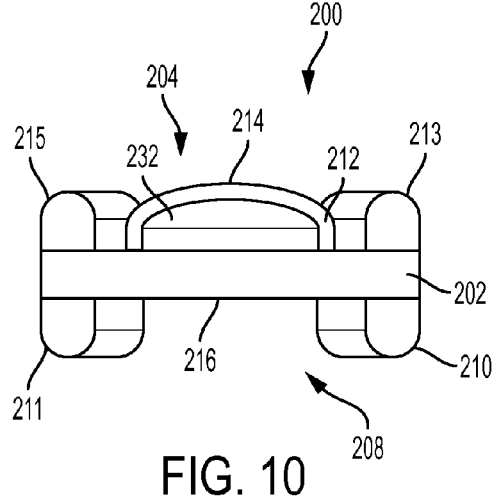
FIG. 10 illustrates a second end view of the oral appliance of FIG. 8

FIGS. 8-10 illustrate various views of another exemplary implementation of an oral appliance 200 configured for stabilizing a subject during radiation therapy. In some implementations, the oral appliance 200 may comprise a body 202, a handle 218, and/or other components. The body 202 may be configured to be secured within the subject's mouth in an as-used position of the oral appliance 200 (e.g., the same or similar to that shown in FIG. 16). By way of non-limiting example, the body 202 may be substantially U-shaped and/or otherwise configured to conform to one or more of the maxillary dental arch, mandibular dental arch, palate, and/or other parts of a subject's mouth.

The body 202 may comprise a first end 224, a second end 226 opposite the first end 224, a first side 228, a second side 230 opposite the first side 228, a first portion 204, a second portion 208 opposite the first portion 204, a tongue positioning component 212, and/or other components. In some implementations, the handle 218 may comprise a proximal end 219, a distal end 220 opposite the proximal end 219, and/or other components. In some implementations, the proximal end 219 of the handle 218 may be attached to or unitarily formed with the first end 224 of the body 202. It is noted that although a registration component (e.g., similar to registration component 122 in FIG. 1) is omitted from the implementations of oral appliance 200 in FIG. 8-FIG. 10, this is for illustrative purposes only and is not to be considered limiting. By way of non-limiting example, the distal end 219 of the handle 218 may include a registration component the same or similar to registration component 122 in FIG. 1.

In some implementations, the tongue positioning component 212 may be the same or similar to tongue positioning component 112 as shown in the implementation of oral appliance 100 in FIG. 1-FIG. 7. By way of non-limiting illustration in FIG. 10, the tongue positioning component 212 of oral appliance 200 may include a cavity 232. The cavity 232 may be formed by a first sidewall 214, a second sidewall 216, and/or other sidewalls.

Oral appliance 200 may be configured to displace both maxillary teeth and/or gums and mandibular teeth and/or gums of a subject away from the body 202 and/or tongue positioning component 212 of the oral appliance 200 when in an as-used position within the subject's mouth, and/or facilitate other intraoral tissue positioning. The first portion 204 may include one or more protrusions configured to engage one or more maxillary teeth and/or gums of the subject in the as-used position. The second portion 208 may include one or more protrusions configured to engage one or more mandibular teeth and/or gums of the subject in the as-used position. By way of non-limiting example, the second portion 208 of the body 202 may include a first protrusion 210, a second protrusion 211, and/or other protrusions. The first portion 204 of the body 202 may include a third protrusion 213, a fourth protrusion 215, and/or other protrusions.

In the current implementation shown, although the first protrusion 210, second protrusion 211, third protrusion 213, and/or fourth protrusion 215 are depicted as having substantially the same or similar thicknesses, this is for illustrative purposes only and is not to be considered limiting. For example, individual thicknesses of the protrusions may be varied as needed to achieve desired displacement of one or both of the maxillary teeth and/or gums, and/or mandibular teeth and/or gums, from the body 202 and/or tongue positioning component 212 of the oral appliance 200 when in the as-used position.

Figure 11:
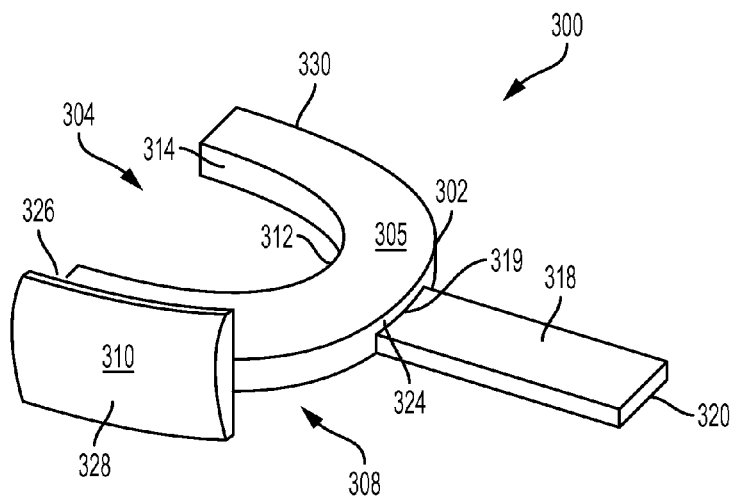
FIG. 11 illustrates still another exemplary implementation of an oral appliance configured for stabilizing a subject during radiation therapy.
Figure 12:
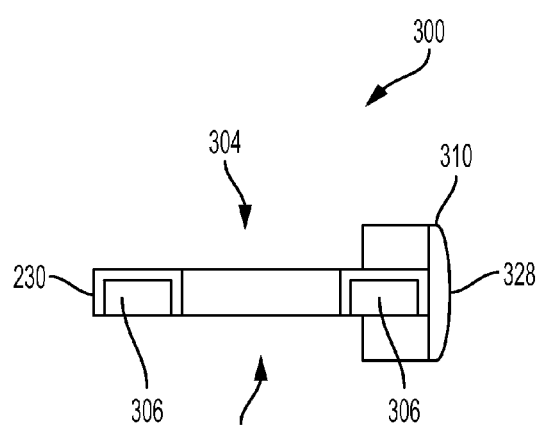
FIG. 12 illustrates an end view of the oral appliance of FIG. 11.
Figure 13:
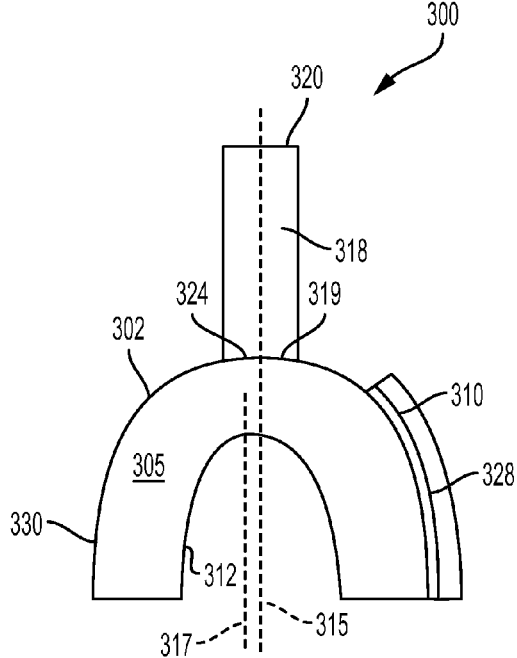
FIG. 13 illustrates a top view of the oral appliance of FIG. 11.

FIGS. 11-13 illustrate various views of yet another exemplary implementation of an oral appliance 300 configured to facilitate stabilizing a subject during radiation therapy. In some implementations, the oral appliance 300 may comprise a body 302, a handle 318, and/or other components. The body 302 may be configured to be secured within a subject's mouth in an as-used position of the oral appliance 300 (e.g., the same or similar to that shown in FIG. 16). By way of non-limiting example, the body 302 may be substantially U-shaped and/or otherwise configured to conform to one or more of the maxillary dental arch, mandibular dental arch, palate, and/or other parts of a subject's mouth.

The body 302 may comprise a first end 324, a second end 326 opposite the first end 324, a first side 328, a second side 330 opposite the first side 328, a first portion 304, a first surface 305, a second portion 308 opposite the first portion 304, a tongue positioning component 312, and/or other components. In some implementations, the handle 318 may comprise a proximal end 319, a distal end 320 opposite the proximal end 319, and/or other components. In some implementations, the proximal end 319 of the handle 318 may be attached and/or unitarily formed with the first end 324 of the body 302. It is noted that although a registration component (e.g., similar to registration component 122 in FIG. 1) is omitted from the implementation of oral appliance 300 in FIGS. 11-13, this is for illustrative purposes only and is not to be considered limiting. By way of non-limiting example, the distal end 320 of the handle 318 may include a registration component the same or similar to registration component 122 in FIG. 1.

In some implementations, the oral appliance 300 may be configured to displace one or more of the subject's cheeks from the body 302 with the oral appliance 300 in the as-used position, and/or facilitate other intraoral tissue positioning. In some implementations, displacing individual cheeks from the body 302 may facilitate displacing soft tissues of the cheeks from the buccal surfaces of one or more mandibular and/or maxillary teeth. Such positioning may be desired to prevent inadvertent injury to soft tissue of a cheek from inadvertently heated restoration and/or to isolate the cheek generally when treating cancers of the cheek. By way of non-limiting example, displacing a subject's cheek may be facilitated by one or more lateral protrusions positioned on one or more sides of the body 302 that may be configured to displace a given cheek away from the teeth.

In some implementations, the oral appliance 300 may include a first lateral protrusion 310 and/or other lateral protrusions. The first lateral protrusion 310 may be disposed on the first side 328, second side 330, first end 324, and/or second end 326 of the body 302. The figure currently shows the first lateral protrusion 310 disposed on the first side 328 of the body. This implementation may provide an exemplary technique for isolating right mandibular and/or maxillary teeth from soft tissues of the subject's mouth including, but not limited to, the tongue and/or inner surface of the right cheek.

Although the first lateral protrusion 310 is shown disposed on the first side 328 of the body 302, this is for illustrative purposes only and is not to be considered limiting. By way of non-limiting example, alternatively or in addition to the provision of a first lateral protrusion 310 on the first side 328, a second lateral protrusion (not shown) may be disposed in a mirrored configuration on the second side 330 of the body 302. Other configurations and/or positions of one or more lateral protrusions are also contemplated. In some implementations, the provision of one or more lateral protrusions may be employed in an implementation of an oral appliance including one or more protrusions configured to displace teeth and/or gums from the body as well.

In FIG. 12, the first lateral protrusion 310 may have a producing sidewall. The first lateral protrusion 310 may be configured to displace the subject's right cheek a distance equivalent to a thickness of the sidewall when in the as-used position.

The first portion 304 of the body 302 may include a first surface 305 and/or other components. The first surface 305 may be configured to engage one or more maxillary teeth and/or gums of the subject in the as-used position. The second portion 308 of the body 302 may include a channel 306 and/or other components. The channel 306 may be configured to conform to the mandibular dental arch of a subject.

In some implementations, the tongue positioning component 312 of the oral appliance 300 may comprise a cutout section formed by a curved sidewall 314. The current implementation of the tongue positioning component 312 may be configured to position the subject's tongue without substantial restriction as compared to the implementations of tongue positioning component 112 and/or 212, including cavities that seat the user's tongue.

In some implementations, the tongue positioning component 312 may be configured to displace the subject's tongue away from a side of the body 302. By way of non-limiting illustration in FIG. 13, the tongue positioning component 312 may be disposed in an off-center position from an imaginary centerline 315 of the oral appliance 300. For example a second imaginary centerline 317 of the tongue positioning component 312 may be displaced a distance from the centerline 315 of the oral appliance 300. This implementation may provide an exemplary technique to isolate the right mandibular teeth and/or gums, and/or maxillary teeth and/or gums, from the tongue and/or right cheek. Such isolation may include displacing the tongue away from the right mandibular and/or maxillary teeth, as may be facilitated by the disposition of the centerline 317 of the tongue positioning component 312 with respect to the centerline 315 of the oral appliance 300.

Figure 14:
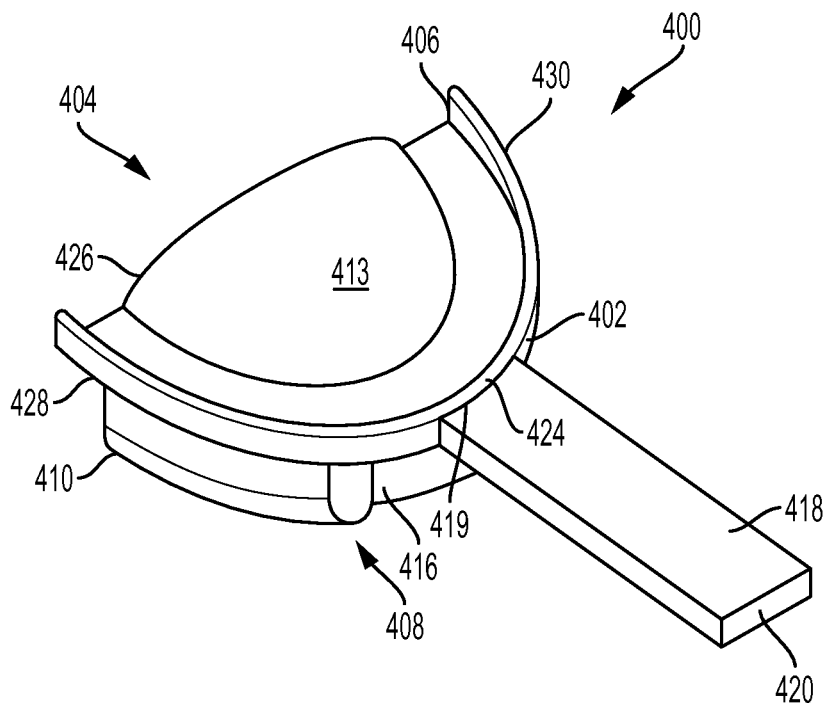
FIG. 14 illustrates another exemplary implementation of an oral appliance configured for stabilizing a subject during radiation therapy.
Figure 15:
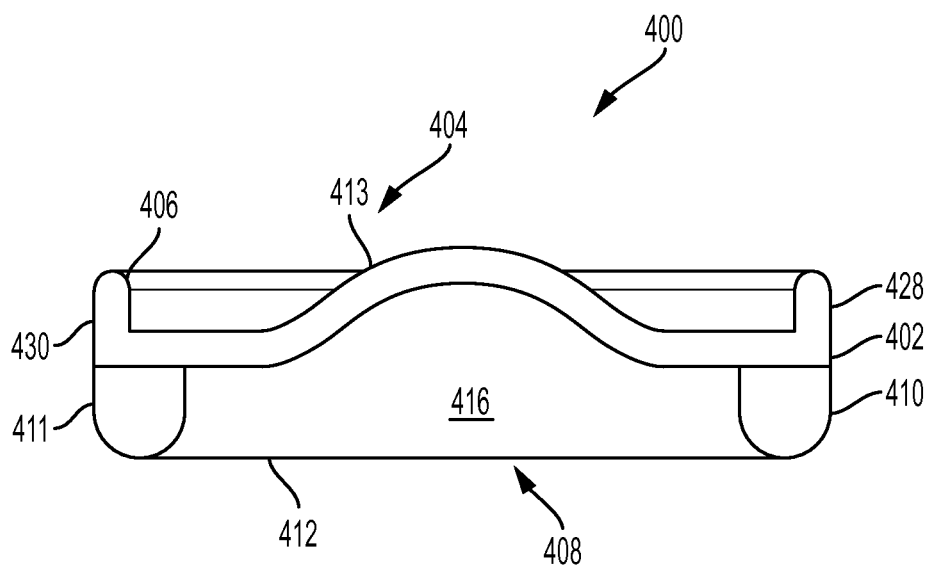
FIG. 15 illustrates a rear view of the oral appliance of FIG. 14.

FIG. 14 and FIG. 15 illustrate various views of still another exemplary implementation of an oral appliance 400 configured to facilitate stabilizing a subject during radiation therapy. In some implementations, the oral appliance 400 may comprise a body 402, a handle 418, and/or other components. The body 402 may be configured to be secured within the subject's mouth in an as-used position of the oral appliance 400 (e.g., the same or similar to that shown in FIG. 16). By way of non-limiting example, the body 402 may be substantially U-shaped and/or otherwise configured to conform to one or more of the maxillary dental arch, mandibular dental arch, palate, and/or other parts of the subject's mouth.

The body 402 may comprise a first end 424, a second end 426 opposite the first end 424, a first side 428, a second side 430 opposite the first side 428, a first portion 404, a second portion 408 opposite the first portion 404, a tongue positioning component 412 (see, e.g., FIG. 15), and/or other components. In some implementations, the handle 418 may comprise a proximal end 419, a distal end 420 opposite the proximal end 419, and/or other components. In some implementations, the proximal end 419 of the handle 418 may be attached and/or unitarily formed with the first end 424 of the body 402. It is noted that although a registration component (e.g., registration component 122 in FIG. 1) is omitted from the implementation of oral appliance 400 in FIG. 14 and FIG. 15, this is for illustrative purposes only and is not to be considered limiting. By way of non-limiting example, in some implementations, the distal end 420 of the handle 418 may include a registration component the same or similar to registration component 122 in FIG. 1.

In some implementations, the oral appliance 400 may be configured to displace the subject's mandible and/or tongue from the body 402, the subject's palate, maxillary teeth and/or gums, and/or other parts of the subject's mouth with the oral appliance 400 in the as-used position, and/or to facilitate other intraoral tissue positioning. In some implementations, displacing a subject's mandible from the body 402 may be facilitated by one or more protrusions disposed on the second portion 408 of the body 402. One or more protrusions of the second portion 408 may be configured to engage one or more mandibular teeth and/or gums of the subject.

By way of non-limiting illustration in FIG. 14, the first portion 404 may include a channel 406 configured to conform to the maxillary arch of a subject, a palatal portion 413 configured to engage with the subject's palate in the as-used position, and/or other components.

By way of non-limiting illustration in FIG. 15, the second portion 408 of the body 402 may include a first protrusion 410, a second protrusion 411, one or more other protrusions, and/or other components. The first protrusion 410, second protrusion 411, and/or other protrusions may be configured to engage one or more mandibular teeth of the subject when the oral appliance 400 is in the as-used position.

In some implementations, the tongue positioning component 412 may comprise a tongue depressor 416, and/or other components. The tongue depressor 416 may generally comprise material extending from the body 402 and disposed in an area between and/or adjacent to the first protrusion 410, the second protrusion 411, and/or other protrusions. The tongue depressor 416 may extend from the second end 426 to the first end 424 of the body 402. In use, the tongue positioning component 412 may be configured to receive the subject's tongue in an area between the first protrusion 410 and second protrusion 411 when the oral appliance 400 is in the as-used position. The tongue positioning component 412 may be configured to facilitate positioning the subject's tongue in a predetermined location and/or orientation based on a predetermined displacement from the body 402 based on a thickness of the tongue depressor 416. It is noted that the shape, configuration, thickness, and/or orientation of the tongue depressor 416 may be of the designer's choice and is not to be considered limiting by the current depictions. By way of non-limiting example, the tongue depressor 416 may be angled relative to the first side 428, second side 430, first end 424, and/or second end 426; and/or configured in other ways.

Figure 18:
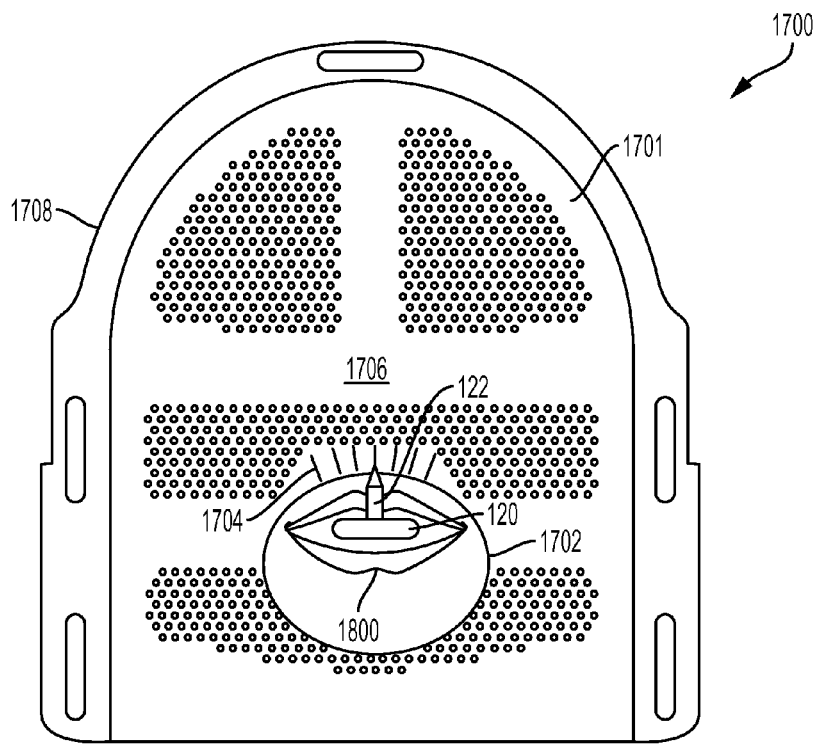
FIG. 18 illustrates an implementation of an oral appliance and head restraint of the system of FIG. 17 in exemplary as-used positions.

FIG. 17 and FIG. 18 illustrate a system 1700 for stabilizing a subject during radiation therapy, in accordance with one or more implementations. The system 1700 may include one or more of a head restraint 1701, an oral appliance (e.g., one or more of oral appliance 100, oral appliance 200, oral appliance 300, oral appliance 400, and/or other implementations of an oral appliance), and/or other components. The head restraint 1701 may be configured to receive a subject's head, neck, face, and/or other body parts in a second as-used position of the head restraint 1701. The head restraint 1701 may comprise a first surface 1706, a second surface opposite the first surface (not shown in FIG. 17 or 18), a mouth opening 1702, a mounting component 1708, and/or other components. The first surface 1706 may be configured to engage at least a portion of the subject's face in a second as-used position of the head restraint 1701. The mouth opening 1702 may comprise, for example, an aperture communicating between the first surface 1706 and second surface. The mouth opening 1702 may be positioned to align with the mouth of the subject when the head restraint 1701 is in the second as-used position. The mounting component 1708 may facilitate mounting the head restraint 1701 to a treatment table (not shown) and/or other structure.

The head restraint 1701 may comprise a thermally responsive material and/or other materials. The head restraint 1701 may be custom formed to a head and/or face of a subject by heating the material and forming an impression of the subject face and/or head. By way of non-limiting example, the head restraint 1701 may comprise thermally responsive material such as a thermo-plastic, a thermo-plastic composite, and/or other material.

A concurrent use of an oral appliance with the head restraint 1701 may facilitate stabilizing the subject's mouth and/or tongue during radiation therapy. For illustrative purposes, oral appliance 100 will be referenced with respect to the system 1700 in FIG. 17 and FIG. 18. It is noted that oral appliance 100 is not shown in its entirety in FIGS. 17 and 18. Instead, the handle 118 is depicted extending from a subject's 1800 mouth to illustrate an exemplary as-used positon of the oral appliance 100 in the subject's mouth.

FIG. 18 illustrates an implementation of the system 1700 showing a front plan view of the oral appliance 100 and head restraint 1701 in respective exemplary as-used positions with respect to the subject 1800. By way of non-limiting example, the subject's head and/or face may be positioned within the head restraint 1701 in such that the handle 118 may protrude though the mouth opening 1702 of the head restraint 1701 (also shown in FIG. 17). In some implementations, the head restraint 1701 may include registration indicia 1704 disposed on a surface of the head restraint 1701 adjacent the mouth opening 1702. The registration indicia 1704 may comprise one or more markings and/or other elements. In some implementations, one or more marking may be disposed at predefined gradations, or degrees, around the mouth opening 1702.

In accordance with one or more exemplary as-used positons, a distal end 120 of the handle 118 may protrude from the mouth opening 1702 of the head restraint 1701. A registration component 122 may facilitate visually discerning a position and/or orientation of the oral appliance 100 with respect to the head restraint 1701. By way of non-limiting example, a practitioner may visually discern a position, orientation, and/or alignment of the registration component 122 with respect to the registration indicia 1704 disposed on the head restraint 1701. Radiation therapy may require multiple sessions. It may be desired to orient and stabilize a subject in the same or similar position for one or more sessions using the oral appliance 100 and/or head restraint 1701. One solution to achieve a consistent as-used position of the oral appliance 100 with respect to the as-used position of the head restraint 1701 may be to ensure that the registration component 122 of an oral appliance 100 may be consistently lined-up with the registration indicia 1704.

Figure 19:
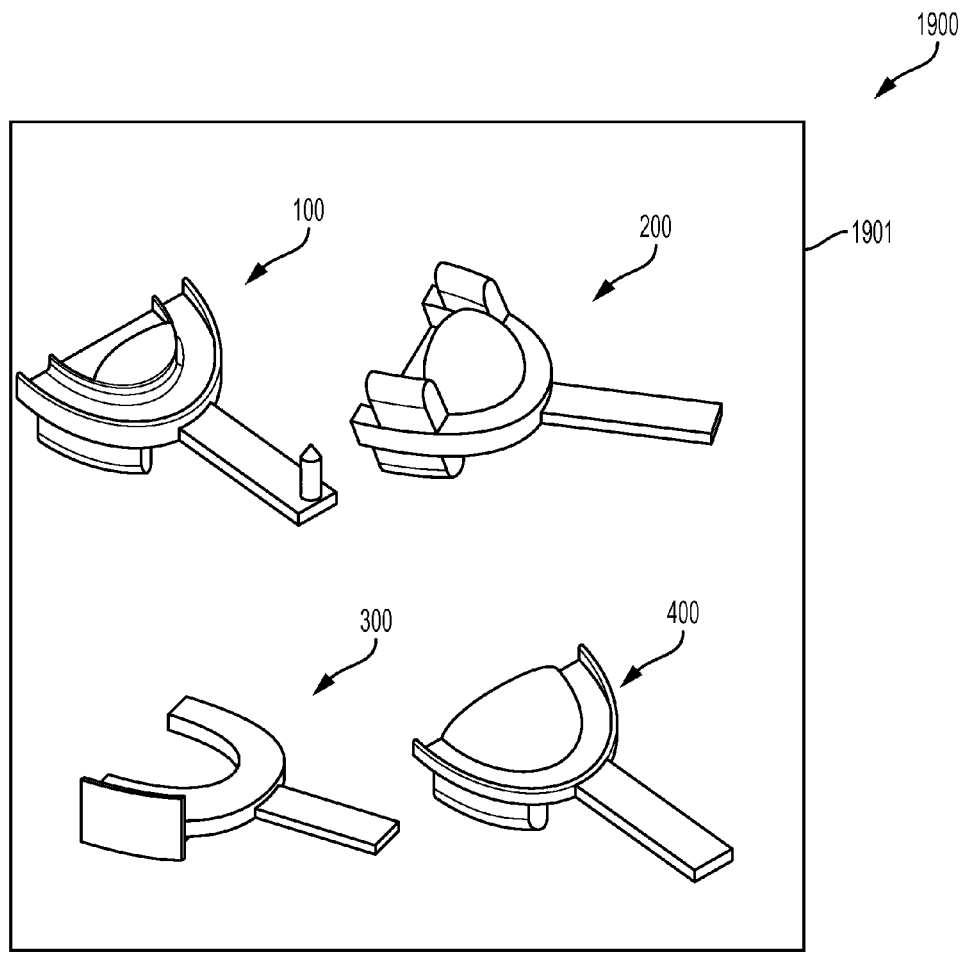
FIG. 19 illustrates a kit of components configured for stabilizing a subject during radiation therapy, in accordance with one or more implementations.

FIG. 19 illustrates an exemplary implementation of a kit 1900 of components configured for stabilizing a subject during radiation therapy, in accordance with one or more implementations. The kit 1900 may comprise one or more oral appliances, one or more head restraints, and/or other components. In some implementations, the kit 1900 may comprise one or more different implementations of an oral appliance (e.g., one or more of oral appliance 100, oral appliance 200, oral appliance 300, oral appliance 400, and/or other implementations), one or more different sizes of one or more implementations of the oral appliance, and/or other components. In some implementations, one or more components of the kit 1900 may be enclosed within a packaging 1901. The packaging 1901 may comprise a sterile packaging and/or other packaging. One or more components of the kit 1900 may be sterilized and included in the sterile packaging 1901. In some implementations, the kit 1900 may be provided to a practitioner in a "ready to use" state. The practitioner may determine a suitable oral appliance to use given the needs of a subject and select as needed from the kit 1900.

Figure 21:
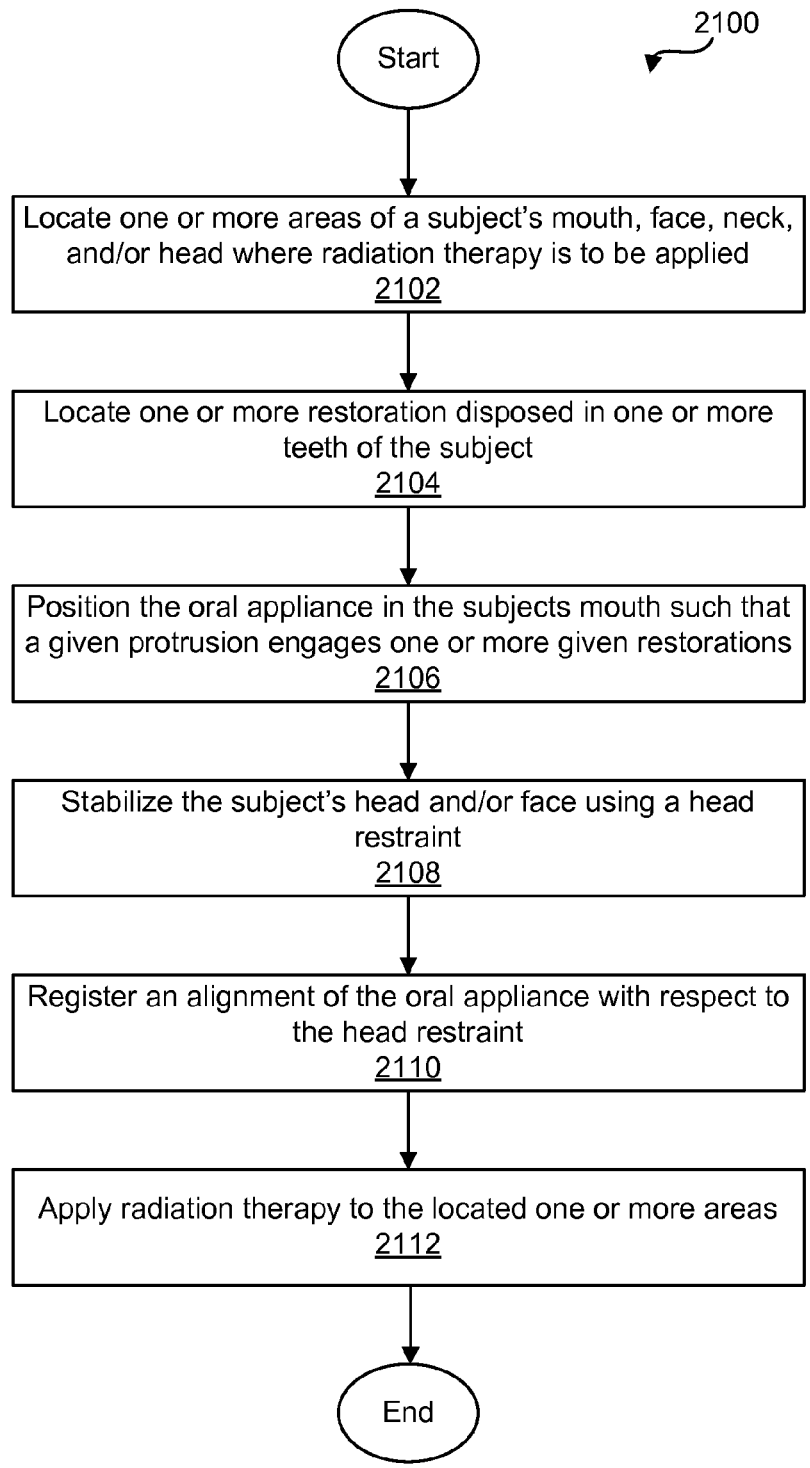
FIG. 21 illustrates a method of stabilizing a subject during radiation therapy, in accordance with one or more implementations.

FIG. 21 illustrates a method 2100 of stabilizing a subject during radiation therapy, in accordance with one or more implementations. The operations of method 2100 presented below are intended to be illustrative. In some embodiments, method 2100 may be accomplished with one or more additional operations not described, and/or without one or more of the operations discussed. Additionally, the order in which the operations of method 2100 are illustrated in FIG. 21 and described below is not intended to be limiting.

In some embodiments, method 2100 may be performed by a practitioner and implemented using one or more oral appliances, one or more head restraints, and/or other components. By way of non-limiting example, the method may be implemented using an oral appliance comprising a body configured to be secured within the subject's mouth in an as-used position of the oral appliance. The body may comprise a first portion configured to engage one or more maxillary teeth of the subject, a second portion configured to engage one or more mandibular teeth of the subject, a tongue positioning component configured to receive the subject's tongue when the oral appliance is in the as-used position and to facilitate positioning the subject's tongue in a predetermined location and/or orientation with respect to the oral appliance when in the as-used position, and/or other components. In some implementations, the oral appliance may be configured such that one or both of the first portion or second portion may include one or more protrusions configured to displace corresponding mandibular teeth or maxillary teeth away from the body of the oral appliance when the oral appliance is in the as-used position. By way of non-limiting example, the method 2100 may be implemented using one or more of oral appliance 100 in FIG. 1, oral appliance 200 in FIG. 8, oral appliance 300 in FIG. 11, oral appliance 400 in FIG. 14, and/or other implementations of an oral appliance.

At an operation 2102, one or more areas of the subject's mouth, face, neck, and/or head where radiation therapy may be applied may be located. By way of non-limiting example, a first area wherein radiation therapy may be applied may be located. In some implementations, areas may be located by CT scan, x-ray, visual inspection, and/or other techniques.

At an operation 2104, one or more restorations disposed in one or more teeth of the subject may be located. By way of non-limiting example, a first restoration disposed on a first tooth of the subject may be located. In some implementations, restorations may be located by CT scan, x-ray, visual inspection, and/or other techniques.

At an operation 2106, the oral appliance may be positioned in the subject's mouth such that a given protrusion engages one or more given restorations. By way of non-limiting example, the oral appliance may be positioned such that a first protrusion of the first portion or second portion engages the first tooth.

At an operation 2108, the subject's head and/or face may be stabilized using a head restraint (e.g., head restraint 1701 in FIG. 17). The head restraint may be mounted to a support surface.

At an operation 2110, an alignment of the oral appliance with respect to the head restraint may be registered. By way of non-limiting example, the oral appliance may include a registration component the same or similar to registration component 122 (shown in FIG. 1 and described herein). The head restraint may include one or more registration indicia the same or similar to registration indicia 1704 (shown in FIG. 17 and described herein).

At an operation 2112, radiation therapy may be applied to one or more located areas where radiation therapy may be applied. Radiation may be applied via an IMRT device and/or other devices or techniques.

Figure 22:
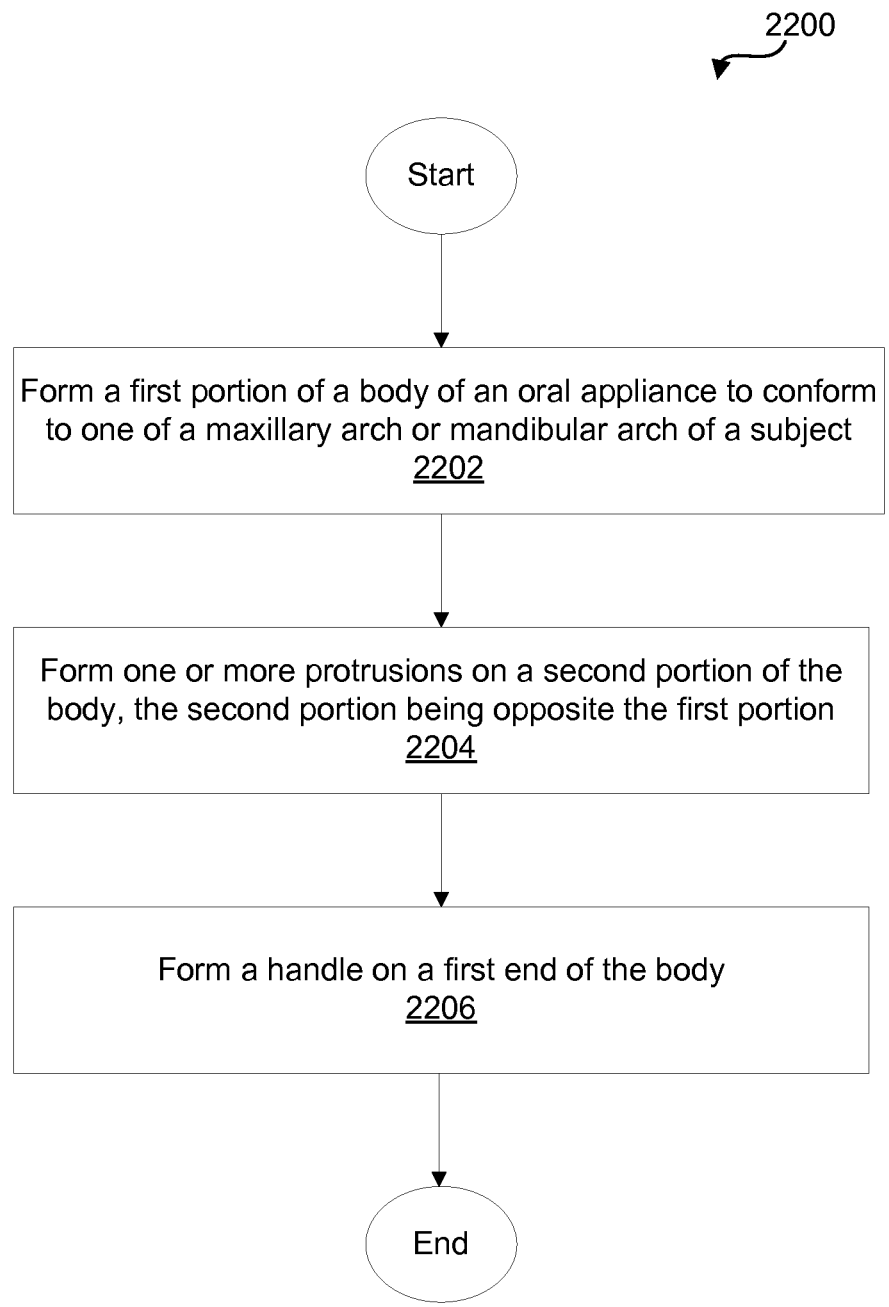
FIG. 22 illustrates a method of fabricating an oral appliance configured for stabilizing a subject during radiation therapy, in accordance with one or more implementations.

FIG. 22 illustrates a method 2200 of fabricating an oral appliance configured for stabilizing a subject during radiation therapy. The operations of method 2200 presented below are intended to be illustrative. In some embodiments, method 2200 may be accomplished with one or more additional operations not described, and/or without one or more of the operations discussed. Additionally, the order in which the operations of method 2200 are illustrated in FIG. 22 and described below is not intended to be limiting. In some implementations, the method 2200 may correspond to forming one or more of oral appliance 100 in FIG. 1, oral appliance 200 in FIG. 8, oral appliance 300 in FIG. 11, oral appliance 400 in FIG. 14, and/or other implementations of an oral appliance.

At an operation 2202, a first portion of a body of the oral appliance may be formed. The first portion may be formed to conform to one of a maxillary arch or mandibular arch of a subject.

At an operation 2204, one or more protrusions may be formed on a second portion of the body. The second portion may be opposite the first portion. The one or more protrusions may be configured to displace corresponding mandibular teeth and/or gums, or maxillary teeth and/or gums, of the subject away from the body when the oral appliance is in an as-used position in the subject's mouth.

At an operation 2206, a handle may be formed on a first end of the body. The handle may be configured to extend from the subject's mouth in the as-used position.

In some implementations, an oral appliance configured for stabilizing a subject during radiation therapy may be fabricated by a method comprising one or more of the steps of method 2200, and/or other steps. By way of non-limiting example, in some implementations, an oral appliance may be fabricated by a method comprising the steps of: forming a first portion of a body of the oral appliance to conform to one of a maxillary arch or mandibular arch of the subject; forming one or more protrusions on a second portion of the body, the second portion may be opposite the first portion, the one or more protrusions may be configured to displace corresponding mandibular teeth or maxillary teeth of the subject away from the body when the oral appliance is in an as-used position in the subject's mouth; forming a handle on a first end of the body, the handle may be configured to extend from the subject's mouth in the as-used position; and/or other steps.

Although the present technology has been described in detail for the purpose of illustration based on what is currently considered to be the most practical and preferred implementations, it is to be understood that such detail is solely for that purpose and that the technology is not limited to the disclosed implementations, but, on the contrary, is intended to cover modifications and equivalent arrangements that are within the spirit and scope of the appended claims. For example, it is to be understood that the present technology contemplates that, to the extent possible, one or more features of any implementation can be combined with one or more features of any other implementation.

What is claimed is:

1. An individually customized oral appliance for positional stabilization of tissues of a tongue, jawbone and/or cheek tissue of a subject while a selected location of an oral irradiation site of the subject is irradiated by a primary beam of radiation during radiation therapy for an oncological treatment, the oral appliance comprising:

a maxillary positioning portion shaped to engage one or ore maxillary teeth of the subject when disposed in an operative position;

a mandibular positioning portion opposite the maxillary portion and shaped to engage one or more mandibular teeth of the subject when disposed in the operative position, where the maxillary positioning portion and the mandibular positioning portion establish a position of the oral appliance relative to the tissues of the tongue jawbone, and/or cheek(s) of the subject; and an individually customized tongue positioning portion to receive the subject's tongue and to stabilize the subject's tongue in a predetermined location and/or orientation with respect to the oral appliance when disposed in the operative position to move the tongue out of the primary beam of radiation that may be directed toward the oral irradiation site to protect or selectively subject the tongue to radiation, where the predetermined location and/or orientation includes a cavity into which the tongue is positioned by the subject, a tongue positioning component, a tongue depressor, a gustatory component, and/or one or more tactile feedback components which are identifiable by the subject using tactile feedback from the tongue, to position the subject's tongue away from the teeth to prevent the tongue from coming into contact with one or more teeth, the primary beam of radiation, and/or backscattered radiation produced from restorations of the teeth, or to hold the tongue in the primary beam of radiation.

2. The oral appliance of claim 1 further comprising a handle extending from a first end of the oral appliance and extending exterior to the subject's mouth when the oral appliance is disposed in the operative position.

3. The oral appliance of claim 1, wherein at least one of the maxillary positioning portion or mandibular positioning portion includes one or more protrusions to displace corresponding mandibular teeth or maxillary teeth away from the oral appliance to facilitate protection of adjacent cheek tissue from the oncological treatment.

4. The oral appliance of claim 1, wherein at least one of the maxillary positioning portion or mandibular positioning portion has a channel defined therein conforming to the corresponding maxillary teeth or mandibular teeth, the channel defining a protective wall on at least one side of the channel between the teeth and adjacent tissues to facilitate protection of adjacent cheek tissue from the oncological treatment.

5. The oral appliance of claim 1, wherein the tongue positioning portion has a cavity defined therein to receive the subject's tongue to facilitate stabilized location of the tongue away from or at the selected location of the oral irradiation site to facilitate stabilization of location of the tongue during the oncological treatment.

6. The oral appliance of claim 5 wherein the cavity includes one or more tactile feedback components to provide tactile feedback to the tongue of the subject when the tongue is correctly positioned and/or oriented in the cavity away from the selected location of the oral irradiation site to facilitate protection of the tongue from the oncological treatment by stabilization of the tongue during the oncological treatment.

7. The oral appliance of claim 1, further comprising one or more lateral protrusions to displace one or both of tissue of the subject's left or right cheek tissues away from the oral appliance, so that incidence of mucositis is reduced to facilitate protection of adjacent cheek tissue from the oncological treatment.

8. The oral appliance of claim 7, wherein the one or more lateral protrusions displace one or both of the subject's left or right cheek tissues from the buccal surfaces of the mandibular teeth and/or maxillary away from the selected location of the oral irradiation site to facilitate protection of adjacent cheek tissue from the oncological treatment.

9. The oral appliance of claim 1 further comprising a head restraint to stabilize the positioning of the head and/or neck of the patient in a predetermined location and/or orientation to assist in stabilization of the relative positions of the tongue, jawbone and/or cheek tissue to allow for repeatedly accurate oncological treatment.

* * * * *